(12) United States Patent
Mountney et al.

(10) Patent No.: US 9,259,200 B2
(45) Date of Patent: Feb. 16, 2016

(54) METHOD AND SYSTEM FOR OBTAINING A SEQUENCE OF X-RAY IMAGES USING A REDUCED DOSE OF IONIZING RADIATION

(71) Applicant: Siemens Aktiengesellschaft, Munich (DE)

(72) Inventors: Peter Mountney, Plainsboro, NJ (US); Andreas Maier, Erlangen (DE); Razvan Ioan Ionasec, Lawrenceville, NJ (US); Jan Boese, Eckental (DE); Dorin Comaniciu, Princeton Junction, NJ (US)

(73) Assignee: SIEMENS AKTIENGESELLSCHAFT, München (DE)

( * ) Notice: Subject to any disclaimer, the term of this patent is extended or adjusted under 35 U.S.C. 154(b) by 264 days.

(21) Appl. No.: 13/654,714

(22) Filed: Oct. 18, 2012

(65) Prior Publication Data

US 2014/0112438 A1    Apr. 24, 2014

(51) Int. Cl.
*A61B 6/06*  (2006.01)
*A61B 6/00*  (2006.01)
*A61B 6/12*  (2006.01)

(52) U.S. Cl.
CPC ............ *A61B 6/5211* (2013.01); *A61B 6/12* (2013.01); *A61B 6/06* (2013.01); *A61B 6/487* (2013.01); *A61B 6/545* (2013.01)

(58) Field of Classification Search
USPC .................................... 378/62, 95
See application file for complete search history.

(56) References Cited

U.S. PATENT DOCUMENTS

| | | | |
|---|---|---|---|
| 5,224,141 A | 6/1993 | Yassa et al. | |
| 6,101,238 A * | 8/2000 | Murthy et al. | 378/62 |
| 7,342,993 B2 | 3/2008 | Besson | |
| 7,505,617 B2 * | 3/2009 | Fu et al. | 382/128 |
| 7,539,284 B2 | 5/2009 | Besson | |
| 7,639,853 B2 | 12/2009 | Olivera et al. | |
| 7,792,249 B2 | 9/2010 | Gertner et al. | |
| 2006/0291711 A1 * | 12/2006 | Jabri | G06T 11/005 382/132 |
| 2008/0242968 A1 * | 10/2008 | Claus | A61B 6/032 600/407 |
| 2010/0198101 A1 * | 8/2010 | Song et al. | 600/547 |
| 2012/0057674 A1 | 3/2012 | Zhang | |
| 2012/0238866 A1 * | 9/2012 | Wang | A61B 6/12 600/424 |
| 2012/0312961 A1 * | 12/2012 | Raleigh | A61B 6/12 250/206 |

* cited by examiner

*Primary Examiner* — Phillip A Johnston
*Assistant Examiner* — Hsien Tsai

(57) ABSTRACT

Methods, systems, and apparatus for obtaining a sequence of x-ray images are disclosed. An object of interest in a first x-ray image is detected and an area of interest, based on a predicted motion of the object of interest, is determined. A second x-ray image of the area of interest is acquired using spatial x-ray modification to control an x-ray to pass through a portion of a patient corresponding to the area of interest.

34 Claims, 8 Drawing Sheets

METHOD AND SYSTEM FOR OBTAINING A SEQUENCE OF X-RAY IMAGES USING A REDUCED DOSE OF IONIZING RADIATION

TECHNICAL FIELD

This specification relates generally to systems and methods for obtaining a sequence of x-ray images, and more particularly to systems and methods for detecting objects in x-ray images.

BACKGROUND

Needle path planning and needle guidance are used in non-invasive surgical procedures in order to avoid critical structure and reduce tissue trauma. During needle path planning DynaCT is used to establish the needle path, and during needle guidance, real time fluoroscopy is used to guide the needle to a target location. Fluoroscopic images and DynaCT are generated using X-rays which are a form of ionizing radiation. To prevent adverse effects from exposure to ionizing radiation the dose is typically managed by restricting the use of these modalities in duration, frequency and space.

Currently, conventional systems achieve a reduction of spatial ionizing radiation dose by allowing for manual alteration of collimator positions by a user. The user is required to identify a particular region of a patient's body and then manually adjust the collimators so that an x-ray image of that particular region will be properly acquired. Such an approach is time consuming, dependent on the user and disruptive to the clinical workflow.

A wide variety of collimators are available, such as collimators with rectangular panels, leaf collimators and semi-transparent collimators. Each type of collimator provides a varying degree of freedom with regard to optimal collimation. Greater flexibility in collimation provides the advantages of being able to reduce the dose of spatial ionizing radiation to which a patient is exposed while acquiring an x-ray image of a particular region of the patient's body. However, greater flexibility in collimation is also accompanied by a complexity in operating the collimators, which decreases the usability of the overall system.

BRIEF SUMMARY OF THE INVENTION

In accordance with various embodiments of the present invention, methods, systems, and apparatus for obtaining a sequence of x-ray images are provided herein. Embodiments of the present invention utilize computer vision techniques to identify an object of interest, such as a needle, predict the location of the object of interest in the next image acquisition and autonomously spatially modify the x-ray to image the predicted location. By altering the x-ray lightbeam to specifically image for the predicted location of the object of interest, the embodiments of the present invention reduce the dose of spatial ionizing radiation that the patient is exposed to without the aforementioned disadvantages of conventional systems.

In one embodiment, an object of interest is detected in a first x-ray image and an area of interest is determined based on a predicted motion of the object of interest. A second x-ray image of the area of interest is acquired using spatial x-ray modification to control an x-ray to pass through a portion of a patient corresponding to the area of interest.

These and other advantages of the present disclosure will be apparent to those of ordinary skill in the art by reference to the following Detailed Description and the accompanying drawings.

DETAILED DESCRIPTION

The present invention is directed to a method and system for obtaining a sequence of x-ray images. Embodiments of the present invention are described herein to give a visual understanding of the x-ray sequence acquisition method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
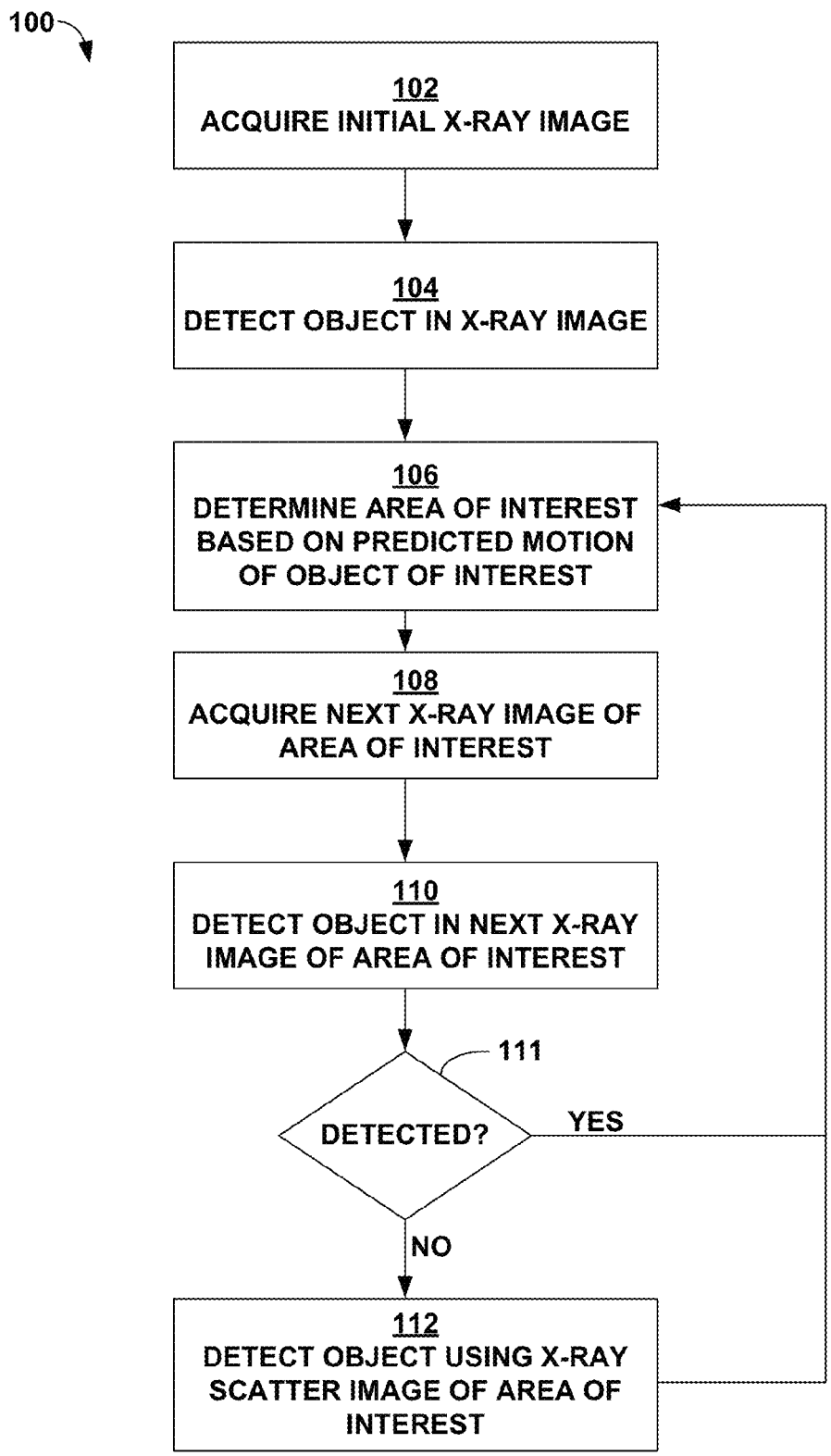
FIG. 1 is a flowchart illustrating a method for obtaining a sequence of x-ray images in accordance with an embodiment of the present invention.
Figure 2:
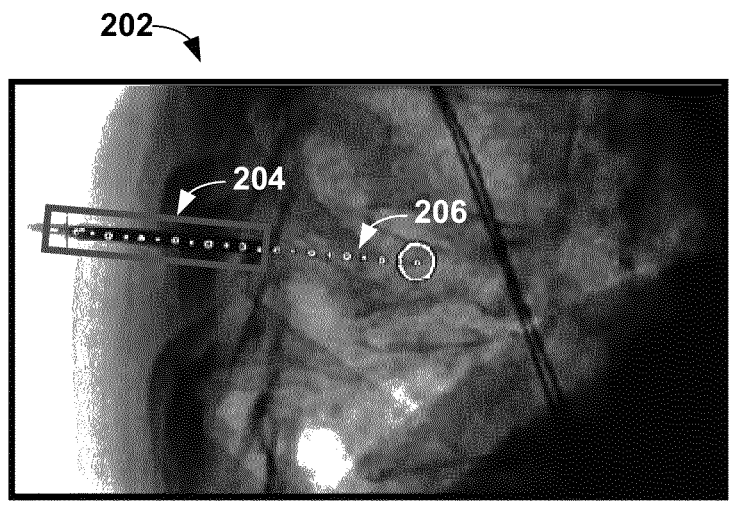
FIG. 2 shows an object of interest detected in an initial x-ray image and a guidance path of the object of interest in accordance with an embodiment of the present invention.

FIG. 1 is a flowchart illustrating a method 100 for obtaining a sequence of images in accordance with an embodiment of the present invention. FIG. 2 shows an object of interest detected in an exemplary x-ray image and a guidance path of the object of interest in accordance with an embodiment of the present invention.

At step 102, an initial x-ray image is acquired. The initial x-ray image can be acquired as one of a sequence of fluoroscopic images. For example, the initial x-ray image can be acquired in real-time as part of a sequence of fluoroscopic images used for needle guidance in a medical procedure. The initial x-ray image can be acquired using an x-ray scanning device, such as a C-arm x-ray image acquisition device. As illustrated in FIG. 2, an x-ray image 202 of a particular portion of a patient's anatomy is acquired.

At step 104, an object of interest 204 is detected in an initial x-ray image 202. The object of interest 204 can be defined as a specific tool, a region of anatomy or any target region in the x-ray image 202. As shown in FIG. 2, the object of interest 204 is a needle within an anatomical region of a patient's body.

According to an advantageous embodiment, a learning based method can be used for autonomous detection of the object of interest 204, or, for purposes of discussion, a needle in the x-ray image 202. Such autonomous detection can identify the location and orientation of the object of interest 202 in the x-ray image 202. When the object of interest 202 is a needle, it can move in a three-dimensional space with six degrees of freedom. The needle's location and orientation in the x-ray image 202 is defined by two points (x,y) in the x-ray image 202. Although the needle is free to move with six degrees of freedom, only the location information is required for spatial x-ray modification. In an embodiment of the present invention, prior knowledge of the needle's position can also be used to reduce search space and false positive detection.

The needle is a high contrast object and may have a varied visual appearance with respect to varying imaging devices and imaging device parameterization. Learning based methods can be trained to be robust to noise and capable of handling large variations in appearance. Such learning based methods are trained on a set of example data. The training data can be manually annotated or synthetically generated data. The manually annotated training data contains a wide variety of needle orientations and locations within an x-ray image. Synthetic data is generated in the form of Digitally Reconstructed Radiograph (DRR). Rays are traced through a computed tomography (CT) scan of a needle to generate synthetic projection images. The training data can also include real and synthetically generated examples of the appearance of a needle occluded by collimators. In addition, the training data includes images without a needle to enable proper classification of non-object regions.

To handle the needle's large variations in appearance, a probabilistic boosting tree (PBT) can be implemented for needle detection. The PBT is trained on a set of example training data in order to learn needle features. The training process for the PBT generates a decision tree which contains a number of tests based on needle features. The training data is divided into sub-trees within the PBT decision tree according to various needle features. The leaf nodes of the resulting PBT decision tree thereby contain a probabilistic distribution of classes of object (i.e. needle) regions of an x-ray image and non-object regions of an x-ray image.

At runtime, prior to classifying an image patch of the image 202 to detect the object of interest 204, the number of false positives can be reduced by applying a steerable filter to the x-ray image 202 in order to identify regions of high contrast, which results in a reduction of the search space as well as increasing computational performance. Image features, such as Haar features, are extracted from image templates identified by the steerable features. Such features are fed into the PBT to classify the image patch as either being in the object of interest 204 or not the object of interest. The 2D position of the needle in the fluoroscopic image is estimated using the classified image patches.

Also, at runtime, prior to classifying an image patch of the image 202 to detect the object of interest 204, a low probability region of the x-ray image 202 can be determined based on information related to a guidance path 206 of the object of interest 204. The low-probability region can be removed from a search space of the PBT. In addition, information about the location of the collimators and semi-transparent collimators can be incorporated as prior knowledge to further reduce the search space and increase performance.

In order to detect the object of interest 204 in the x-ray image 202, Haar features are extracted from image patches of the x-ray image 202 and the PBT determines a probability score for each image patch. The image patch having the highest probability score is determined to be the position of the object of interest 204 in the x-ray image 202.

In alternative embodiments, object detection may be performed according to (1) user input via a computer console, (2) user input via a device attached to an external surface of a patient and visible in x-ray and (3) by a user's eye gaze.

Figure 3:
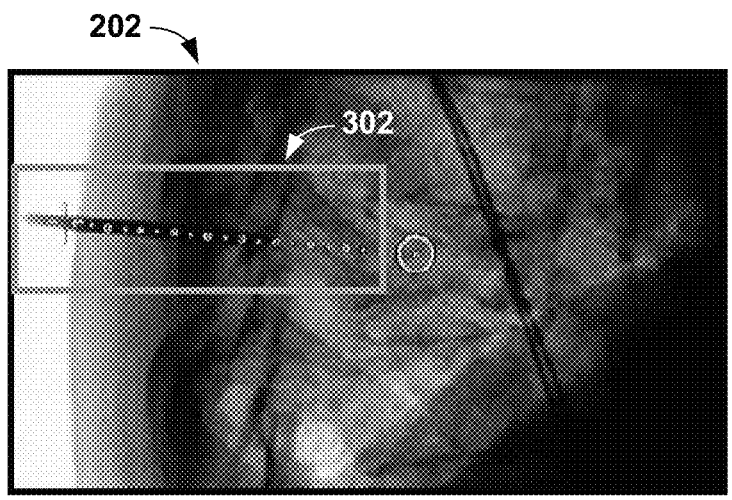
FIG. 3 shows an area of interest based on a predicted motion of an object of interest in accordance with an embodiment of the present invention.

Returning to FIG. 1, at step 106, an area of interest is determined based on a predicted motion of the object of interest. FIG. 3 shows an area of interest 302 detected in the x-ray image 202.

When the object of interest 204 (e.g. needle) is static and the imaging device is static, an area of interest surrounding the needle will be easy to define and can be done manually. However, if either the needle or imaging device are in motion, the size of the area of the interest must account for uncertainty caused by the motion.

When the needle is moving in the x-ray image 202, a next location of the needle can be predicted by predicting the needle's motion. Predicting the needle's motion allows for minimizing a size of the area of interest 302, which is defined as a region surrounding the predicted next location of the needle. By minimizing the size of the area of interest 302 through motion prediction, a minimal dose of ionized radiation will be required for an x-ray image of the area of interest 302.

In one possible implementation, the needle's motion can be predicted in a 2D fluoroscopic image using any of the following methods: the Extended Kalman Filter model, a Particle Filter model (or its variants), or a Learnt Motion models. In addition, these motion models can incorporate prior information from a needle path planning phase to reduce uncertainty of the needle's motion. Additionally, it is also feasible to alter the frequency at which x-ray images are captured, such that x-ray images are captured at a higher rate for an object of interest that is moving at a rapid pace.

In acquisition of a 3D Dyna CT volume, a set of two-dimensional (2D) x-ray images is taken in order to reconstruct the scanned volume. This is usually performed in a rotation that covers 180 degrees, plus a fan angle, because every voxel reconstructed inside the scanned volume has to be observed from at least 180 degrees. If collimation is performed, the volume that can be reconstructed is also reduced. As the motion of the arm and the intrinsic parameters of the imaging device are typically known, the uncertainty in the imaged area is less.

In another possible implementation, the area of interest may also be estimated in 3D by using multiple geometry techniques and epipolar constraints in conjunction with input from robotic systems associated with control of the imaging device. Needle positions in previous projections describe the position of the needle in a two-dimensional (2D) format. As each view is calibrated, each respective 2D needle position defines a cone with the source at the tip and the area on the detector as the base. An intersection of multiple such cones describes an approximate 3D position of the needle. The approximate 3D position becomes further refined by each additional projection, and adaptive control is regularized in such a way that at least the approximate 3D position of the needle and a small area around it can be reconstructed as the area of interest.

Figure 4:
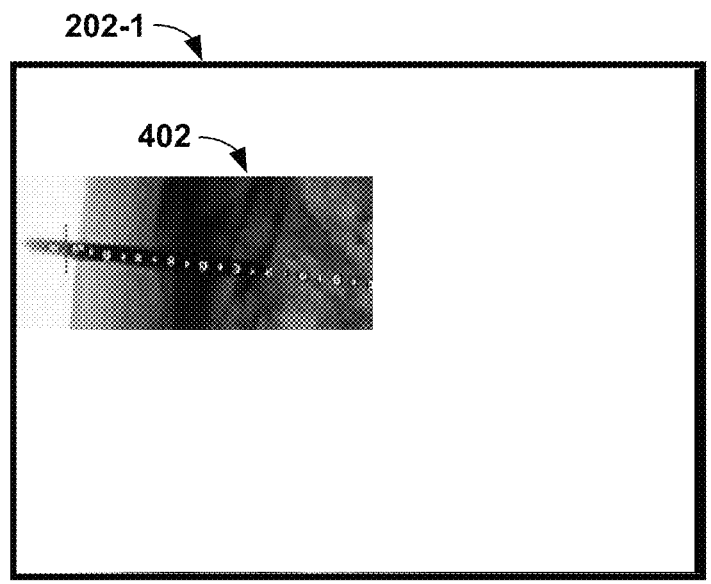
FIG. 4 shows a next x-ray image of an area of interest in accordance with an embodiment of the present invention.

Returning to FIG. 1, at step 108, a next x-ray image 402 of the area of interest 302 is acquired using spatial x-ray modification to control an x-ray to pass through a portion of a patient corresponding to the area of interest 302. FIG. 4 shows the next x-ray image 402 of the area of interest 302 in accordance with an embodiment of the present invention. The next x-ray image 402 of the area of interest 302 is shown in FIG. 4 relative to the boundaries 202-1 of the initial x-ray image 202 in order to demonstrate that the size of the next x-ray image 402 of the area of interest 302 is significantly smaller than the size of the initial x-ray image 202, thereby requiring a smaller dose of ionized radiation.

Spatial x-ray modification is the process of controlling the direction in which the x-ray lightbeam will travel such that the x-ray lightbeam will only pass through the portion of a patient corresponding to the area of interest 302. One approach for controlling the direction of the x-ray lightbeam is to alter a shape and/or a position of the x-ray lightbeam by changing a collimator of an imaging device. Another approach involves the use of one or more semitransparent collimators of the imaging device to constrain the x-ray lightbeam's direction(s). In yet another approach, an angulation of a C-arm of the imaging device and/or a rotation of a detector of the imaging device can be changed to influence the x-ray lightbeam's direction. In yet another approach, a position of the table upon which the patient rests, can be changes to further control the direction of the x-ray lightbeam. These approaches can be used individually or in any combination to implement the spatial x-ray modification. It is understood that these approaches are not limiting and other approaches for spatial x-ray modification may be used as well.

Figure 8:
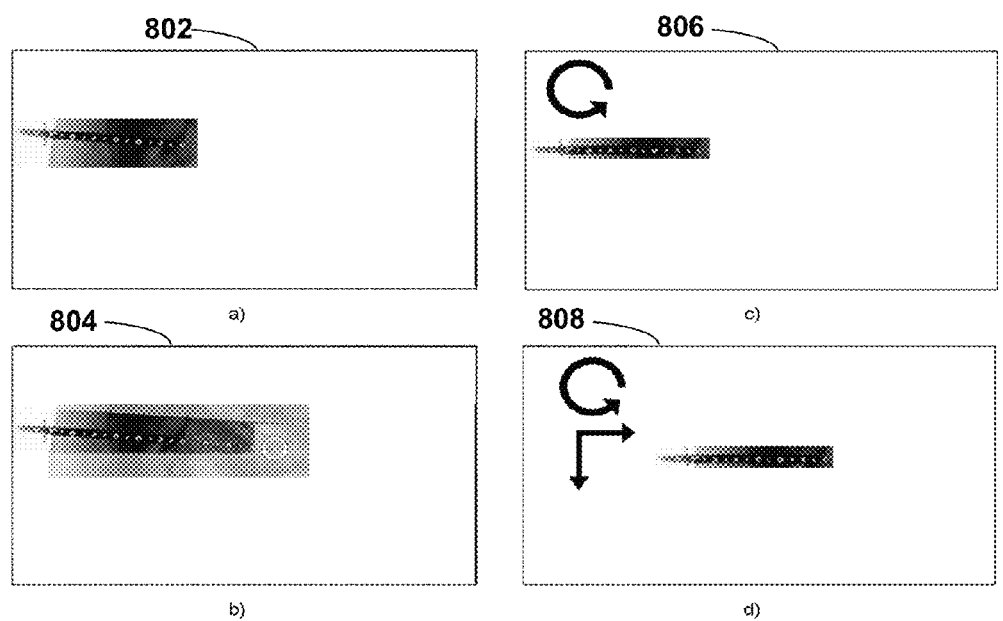
FIG. 8 provides exemplary x-ray images captured via spatial x-ray modification in accordance with an embodiment of the present invention.

FIG. 8 provides exemplary x-ray images 802, 804, 806, 808 captured via the various approaches to spatial x-ray modification mentioned above. X-ray image 802 is an x-ray image resulting from altering a shape and/or a position of an x-ray lightbeam by changing a collimator of an imaging device. X-ray image 804 is an x-ray image resulting from the use of three semitransparent collimators of an imaging device to constrain a x-ray lightbeam's direction(s). X-ray image 806 is an x-ray image resulting from changing an angulation of a C-arm of the imaging device in order to influence the x-ray lightbeam's direction. Such an approach may be applied during acquisition imaging for the process of reconstruction volumes such as DynaCT. This results in a scan that has an object-dependent collimation in each view. The collimation is adaptively reconfigured throughout the complete scan. One input parameter for the adaptive control is obtained from the image by needle detection. However, this may result in an acquisition that does not fulfill the data completeness condition that each voxel that should be reconstructed at least 180 degrees of angular views have to be acquired. X-ray image 808 is an x-ray image resulting from changing a position of the table upon which the patient rests.

Figure 5:
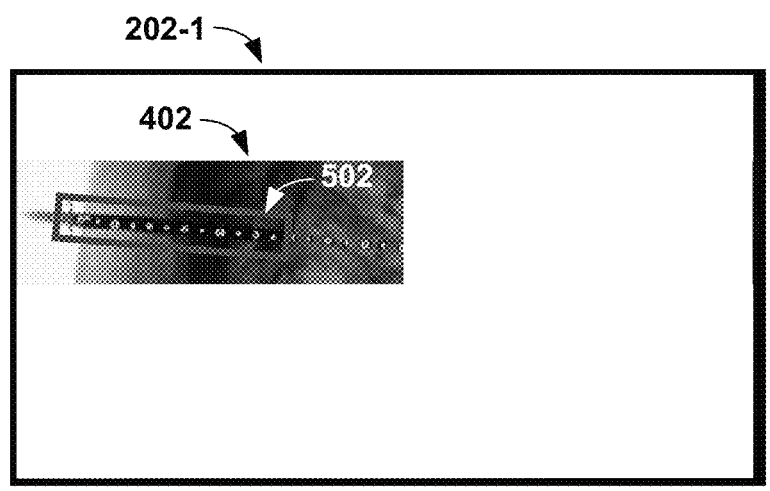
FIG. 5 shows an object of interest detected in a next x-ray image of an area of interest in accordance with an embodiment of the present invention.

Returning to FIG. 1, at step 110, the object of interest is detected in the next x-ray image 402 of the area of interest 302. FIG. 5 illustrates the object of interest 502 detected in a next x-ray image 402. The object of interest 502 can be detected in the next x-ray image 402 using a learning based object detection approach described above with respect step 104.

At step 111, it is determined if the object of interest 502 is successfully detected in the next x-ray image 402. If it is determined that the object of interest 502 was successfully detected, the method 100 returns to step 106, and an area of interest is defined based on the predicted motion of the object of interest 502.

Figure 6A:
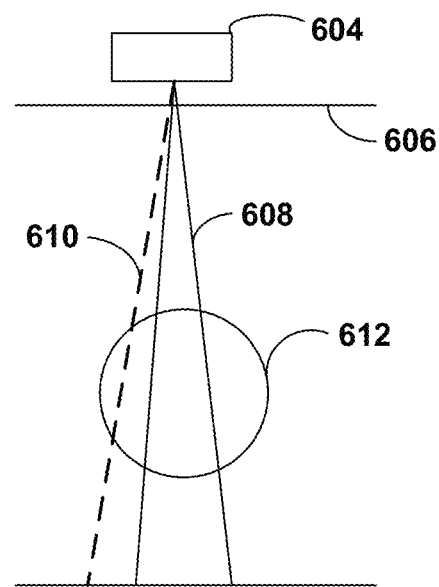
FIG. 6A shows a diagram of photons scattered beyond a collimated area defined for an x-ray image in accordance with an embodiment of the present invention.
Figure 6B:
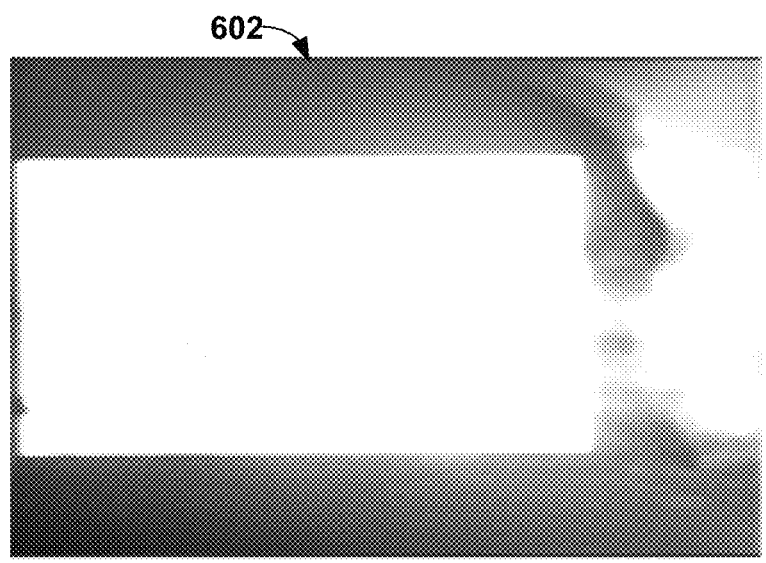
FIG. 6B shows an x-ray scatter image in accordance with an embodiment of the present invention.

However, if it is determined at step 111 that the object of interest 502 is not successfully detected in the next x-ray image 402, the method proceeds to step 112. At step 112, the object of interest 502 is detected in an x-ray scatter image. FIG. 6A shows a diagram of photons scattered beyond a collimated area defined for an x-ray image. FIG. 6B shows an exemplary x-ray scatter image 602 of an area beyond a collimated area defined for an x-ray image.

As the object of interest can be an object of high contrast, it is visible in an x-ray scatter image 602 due to photons that are scattered by collimator edges. The position of the collimator 606 defines a collimated area for an irradiated cone 608 from an x-ray source 604 to pass through an object 612 (such as a patient's body). Although collimation should cause all x-ray photons to be absorbed, the edges of the collimator 606 are themselves a source of scattered x-ray photons 610. In other words, x-ray photons that hit the collimator edges are scattered beyond the collimated area defined for the x-ray image. An x-ray scatter image 602 is an image of the scattered photons, and objects that are in an area covered by the collimator 606 may be visible in the x-ray scatter image 602. An x-ray scatter image 602 associated with the x-ray image is generated in order to be used in detection of the object of interest.

Since the signal intensity and also the appearance of the object of interest is somewhat different in the x-ray scatter image 602 than in a full-beam x-ray image, an adapted version of the needle detection algorithm described above uses different training data matched to the x-ray scatter image data. Specifically, the object of interest can be detected in the x-ray scatter image 602 using a PBT trained on annotated training data including x-ray scatter image data.

Once the object is detected using the x-ray scatter image 602, the method, as illustrated in flowchart 100 of FIG. 1, returns to steps 106-112 and steps 106-112 are then repeated resulting in a sequence of x-ray images being acquired. It is understood that steps 106-112 can be repeated any number of times depending on how large of a sequence x-ray images is required. These steps can be repeated in real-time during a surgical procedure to provide needle guidance.

Figure 7:
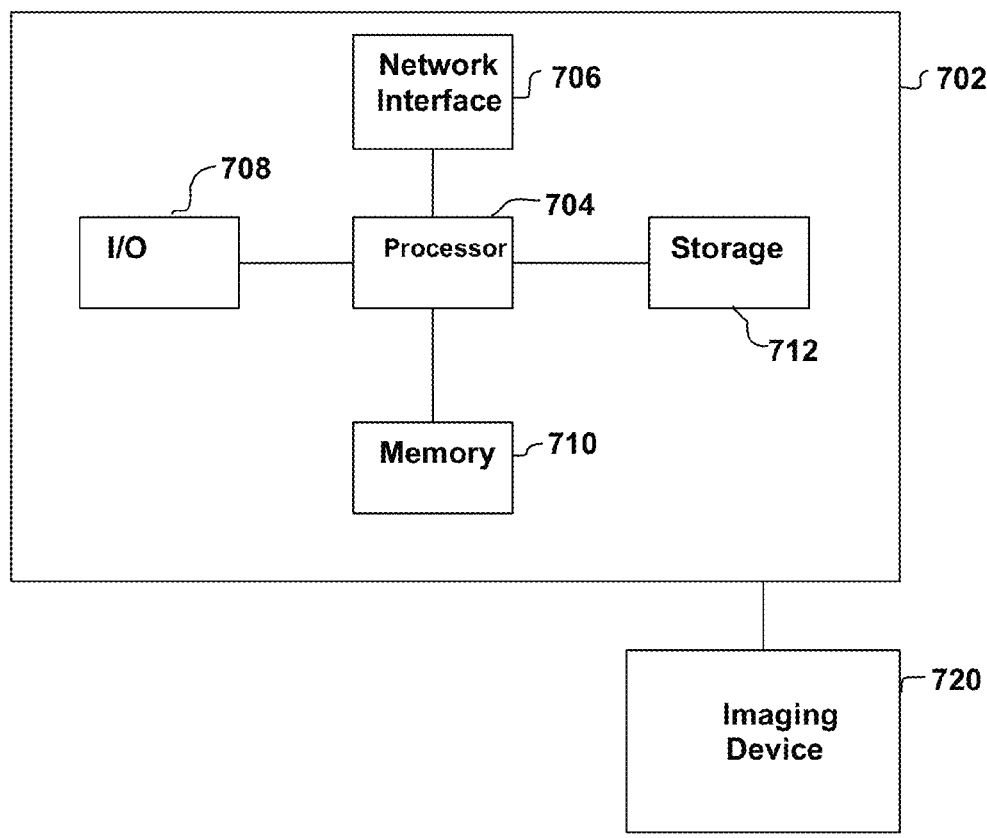
FIG. 7 is a high-level block diagram of a computer capable of implementing the embodiments disclosed herein.

The above-described methods for obtaining a sequence of x-ray images may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIG. 1 may be defined by the computer program instructions stored in the memory 710 and/or storage 712 and controlled by the processor 704 executing the computer program instructions. An imaging device 720, such as a C-arm image acquisition device, can be connected to the computer 702 to input image data to the computer 702. It is possible to implement the imaging device 720 and the computer 702 as one device. It is also possible that the imaging device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for obtaining a sequence of x-ray images, comprising:
    detecting an object of interest in a patient in a first x-ray image;
    determining an area of interest based on a predicted motion of the object of interest;
    acquiring a second x-ray image based on the area of interest determined in the first x-ray image using spatial x-ray modification to control an x-ray to pass through a portion of the patient corresponding to the area of interest, the second x-ray image having a reduced imaging size of the patient relative to the first x-ray image;
    determining whether the object of interest was successfully detected in the second x-ray image; and
    in response to determining that the object of interest was not successfully detected in the second x-ray image:
        generating an x-ray scatter image of a region beyond the area of interest determined in the first x-ray image.

2. The method of claim 1, wherein detecting an object of interest in a first x-ray image comprises:
    automatically detecting the object of interest in the first x-ray image using a probabilistic boosting tree (PBT) trained on annotated training data.

3. The method of claim 2, wherein detecting an object of interest in a first x-ray image further comprises:
    determining at least one low probability region of the first x-ray image based on information related to a guidance path of the object of interest; and
    removing the determined at least one low probability region from a search space of the PBT prior to automatically detecting the object of interest in the first x-ray image using the PBT.

4. The method of claim 2, wherein detecting an object of interest in a first x-ray image further comprises:
    applying a steerable filter to the first x-ray image to identify at least one high contrast region of the first x-ray image; and
    removing the identified at least one high contrast region from a search space of the PBT prior to automatically detecting the object of interest in the first x-ray image using the PBT.

5. The method of claim 1, wherein determining an area of interest based on a predicted motion of the object of interest comprises:
    predicting a next location of the object of interest by predicting a motion of the object of interest; and
    defining the area of interest as a region surrounding the predicted next location of the object of interest.

6. The method of claim 5, wherein predicting a next location of the object of interest by predicting a motion of the object of interest comprises:
    predicting the motion of the object of interest using one of:
        an Extended Kalman Filter model, a Particle Filter model, and a Learnt Motion model.

7. The method of claim 6, wherein the one of the Extended Kalman Filter model, the Particle Filter model, and the Learnt Motion model incorporates prior information regarding a planned path of the object of interest.

8. The method of claim 1, wherein acquiring a second x-ray image of the area of interest using spatial x-ray modification to control an x-ray to pass through a portion of a patient corresponding to the area of interest comprises:
    changing at least one collimator of an imaging device to alter at least one of a shape and a position of an x-ray lightbeam, such that the x-ray lightbeam only passes through the portion of the patient corresponding to the area of interest.

9. The method of claim 1, wherein acquiring a second x-ray image of the area of interest comprises:
    utilizing at least one semitransparent collimator of the image device to constrain the x-ray lightbeam to only pass through the portion of the patient corresponding to the area of interest.

10. The method of claim 1, wherein acquiring a second x-ray image of the area of interest comprises:
    changing at least one of an angulation of a C-arm of the imaging device and a rotation of a detector of the imaging device.

11. The method of claim 1, wherein acquiring a second x-ray image of the area of interest comprises:
    changing a position of a table of the imaging device.

12. The method of claim 1, further comprising:
    detecting the object of interest in the second x-ray image;
    determining a second area of interest based on a second predicted motion of the object of interest detected in the second x-ray image; and
    acquiring a third x-ray image of the second area of interest using spatial x-ray modification to control an x-ray to pass through a portion of the patient corresponding to the second area of interest.

13. The method of claim 1, further comprising:
    in response to determining that the object of interest was not successfully detected in the second x-ray image:
        detecting the object of interest in the x-ray scatter image.

14. The method of claim 13, wherein detecting the object of interest in the x-ray scatter image comprises:
    detecting the object of interest in the x-ray scatter image using a probabilistic boosting tree (PBT) trained on annotated training data comprising x-ray scatter image data.

15. A non-transitory computer readable medium storing computer program instructions for obtaining a sequence of x-ray images, which, when the instructions are executed on a processor, cause the processor to perform operations comprising:
    detecting an object of interest in a patient in a first x-ray image;
    determining an area of interest based on a predicted motion of the object of interest;
    acquiring a second x-ray image based on the area of interest determined in the first x-ray image using spatial x-ray modification to control an x-ray to pass through a portion of the patient corresponding to the area of interest, the second x-ray image having a reduced imaging size of the patient relative to the first x-ray image;
    determining whether the object of interest was successfully detected in the second x-ray image; and
    in response to determining that the object of interest was not successfully detected in the second x-ray image:
        generating an x-ray scatter image of a region beyond the area of interest determined in the first x-ray image.

16. The non-transitory computer readable medium of claim 15, wherein detecting an object of interest in a first x-ray image comprises:
    automatically detecting the object of interest in the first x-ray image using a probabilistic boosting tree (PBT) trained on annotated training data.

17. The non-transitory computer readable medium of claim 16, wherein detecting an object of interest in a first x-ray image further comprises:
   determining at least one low probability region of the first x-ray image based on information related to a guidance path of the object of interest; and
   removing the determined at least one low probability region from a search space of the PBT prior to automatically detecting the object of interest in the first x-ray image using the PBT.

18. The non-transitory computer readable medium of claim 16, wherein detecting an object of interest in a first x-ray image further comprises:
   applying a steerable filter to the first x-ray image to identify at least one high contrast region of the first x-ray image; and
   removing the identified at least one high contrast region from a search space of the PBT prior to automatically detecting the object of interest in the first x-ray image using the PBT.

19. The non-transitory computer readable medium of claim 15, wherein determining an area of interest based on a predicted motion of the object of interest comprises:
   predicting a next location of the object of interest by predicting a motion of the object of interest; and
   defining the area of interest as a region surrounding the predicted next location of the object of interest.

20. The non-transitory computer readable medium of claim 19, wherein predicting a next location of the object of interest by predicting a motion of the object of interest comprises:
   predicting the motion of the object of interest using one of:
      an Extended Kalman Filter model, a Particle Filter model, and a Learnt Motion model.

21. The non-transitory computer readable medium of claim 20, wherein the one of the Extended Kalman Filter model, the Particle Filter model, and the Learnt Motion model incorporates prior information regarding a planned path of the object of interest.

22. The non-transitory computer readable medium of claim 15, wherein acquiring a second x-ray image of the area of interest using spatial x-ray modification to control an x-ray to pass through a portion of a patient corresponding to the area of interest comprises:
   changing at least one collimator of an imaging device to alter at least one of a shape and a position of an x-ray lightbeam, such that the x-ray lightbeam only passes through the portion of the patient corresponding to the area of interest.

23. The non-transitory computer readable medium of claim 15, wherein acquiring a second x-ray image of the area of interest comprises:
   utilizing at least one semitransparent collimator of the image device to constrain the x-ray lightbeam to only pass through the portion of the patient corresponding to the area of interest.

24. The non-transitory computer readable medium of claim 15, wherein acquiring a second x-ray image of the area of interest comprises:
   changing at least one of an angulation of a C-arm of the imaging device of the imaging device and a rotation of a detector of the imaging device.

25. The non-transitory computer readable medium of claim 15, wherein acquiring a second x-ray image of the area of interest comprises:
   changing a position of a table of the imaging device.

26. The non-transitory computer readable medium of claim 15, further comprising:
   detecting the object of interest in the second x-ray image;
   determining a second area of interest based on a second predicted motion of the object of interest detected in the second x-ray image; and
   acquiring a third x-ray image of the second area of interest using spatial x-ray modification to control an x-ray to pass through a portion of the patient corresponding to the second area of interest.

27. The non-transitory computer readable medium of claim 15, further comprising:
   in response to determining that the object of interest was not successfully detected in the second x-ray image:
      detecting the object of interest in the x-ray scatter image.

28. The non-transitory computer readable medium of claim 27, wherein detecting the object of interest in the x-ray scatter image comprises:
   detecting the object of interest in the x-ray scatter image using a probabilistic boosting tree (PBT) trained on annotated training data comprising x-ray scatter image data.

29. A system for obtaining a sequence of x-ray images, comprising:
   means for detecting an object of interest in a patient in a first x-ray image;
   means for determining an area of interest based on a predicted motion of the object of interest;
   means for acquiring a second x-ray image based on the area of interest determined in the first x-ray image using spatial x-ray modification to control an x-ray to pass through a portion of the patient corresponding to the area of interest, the second x-ray image having a reduced imaging size of the patient relative to the first x-ray image;
   means for determining whether the object of interest was successfully detected in the second x-ray image; and
   means for generating an x-ray scatter image of a region beyond the area of interest determined in the first x-ray image in response to a determination that the object of interest was not successfully detected in the second x-ray image.

30. The system of claim 29, wherein the means for determining an area of interest based on a predicted motion of the object of interest comprises:
   means for predicting a next location of the object of interest by predicting a motion of the object of interest; and
   means for defining the area of interest as a region surrounding the predicted next location of the object of interest.

31. The system of claim 29, wherein the means for detecting an object of interest in a first x-ray image comprises:
   means for automatically detecting the object of interest in the first x-ray image using a probabilistic boosting tree (PBT) trained on annotated training data.

32. The system of claim 29, further comprising:
   means for detecting the object of interest in the second x-ray image;
   means for determining a second area of interest based on a second predicted motion of the object of interest detected in the second x-ray image; and
   means for acquiring a third x-ray image of the second area of interest using spatial x-ray modification to control an x-ray to pass through a portion of the patient corresponding to the second area of interest.

33. The system of claim 29, further comprising:
   means for detecting the object of interest in the x-ray scatter image.

34. The system of claim 33, wherein the means for detecting the object of interest in the x-ray scatter image comprises:

means for detecting the object of interest in the x-ray scatter image using a probabilistic boosting tree (PBT) trained on annotated training data comprising x-ray scatter image data.

* * * * *